United States Patent
Donovan

(10) Patent No.: US 7,022,329 B2
(45) Date of Patent: *Apr. 4, 2006

(54) METHOD FOR TREATING NEUROGENIC INFLAMMATION PAIN WITH BOTULINUM TOXIN AND SUBSTANCE P COMPONENTS

(75) Inventor: Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/082,691

(22) Filed: Feb. 25, 2002

(65) Prior Publication Data

US 2003/0165541 A1 Sep. 4, 2003

(51) Int. Cl.
 C07K 19/00 (2006.01)
 C07K 14/33 (2006.01)
 A61K 38/16 (2006.01)

(52) U.S. Cl. .................. 424/239.1; 514/2; 514/12; 530/350; 530/412; 435/68.1; 435/69.1; 435/70.1; 435/320.1; 435/252.3; 435/325; 536/23.1

(58) Field of Classification Search .......... 514/14, 514/12, 2, 825, 885; 424/239.1; 435/68.1, 435/69.1, 70.1, 320.1, 325; 530/350
See application file for complete search history.

(56) References Cited

U.S. PATENT DOCUMENTS 6,063,768 A   5/2000  First
6,500,436 B1 * 12/2002  Donovan ............... 424/239.1

FOREIGN PATENT DOCUMENTS

WO          9416629        7/1994
WO          0121213        3/2001

OTHER PUBLICATIONS

Haberman, Naunyn-Schmiedebergs Arch. Pharmacol 281. 47-56, 1974.
Wiegand et al, Naunyn-Schmiedebergs Arch. Pharmacol 292. 161-165, 1976.
Suzuki et al, Journal of Immunology 163. 2410-2415, 1999.
Spanos et al, Journal of Urology 157. 669-672, 1997.
Foreman, Int. Archs Allergy Appl. Immun. 82. 366-371, 1987.
Columbo et al. Clinical Immunology and Immunopathology 81(1) 68-73, 1996.
Syabbalo. Int J Clin Pract 51(7) 455-462, 1997.
Renner et al. Pharmazie 37. 866, 1982.
Brookoff. Hospital Practice: Chronic Pain. www.hosppract.com, 2000.
Mantyh, Annals New York Acad. of Sciences, 263-270.
Paumet et al, Journal of Immunology (164) 5850-5857, 2000.
Enestrom et al, Scand J Rheumatol (26) 308-313, 1997.
Toyoda et al, Arch Dermatol Res (292) 418-421, 2000.
Pang et al, Urology (47) 436-438, 1996.
Palm et al, J Rheumatol (28) 590-594, 2001.
Besson, Lancet (353) 1610-1615, 1999.

* cited by examiner

*Primary Examiner*—Irene Marx
(74) *Attorney, Agent, or Firm*—Dean G. Stathakis; Martin A. Voet; Joel B. German

(57) ABSTRACT

The present invention relates to methods for treating neurogenic inflammation pain. The methods include administering an effective amount of a composition which includes a *botulinum* toxin component and a substance P component to a patient, thereby treating the neurogenic inflammation pain.

14 Claims, No Drawings

METHOD FOR TREATING NEUROGENIC INFLAMMATION PAIN WITH BOTULINUM TOXIN AND SUBSTANCE P COMPONENTS

BACKGROUND

The present invention relates to methods for treating inflammation pain, for example, neurogenic inflammation pain. In particular, the present invention relates to methods for treating pain using *Clostridial* toxin compositions and methods for making the *Clostridial* toxin compositions.

In recent years attention has been directed toward the interaction between components of the nervous system and target cells of the immune system. Communication between nerve cells and cells which mediate inflammation is demonstrative of such neuroimmune interactions. For example, several studies have demonstrated that mast cells and vascular endothelial cells are often in close contact with nerves and that there may be a functional interaction between these cells and the nervous system. In addition, recent evidence suggests that the neuropeptide substance P is an important mediator in cross talk between nerves and inflammation mediating cells.

Mast cells and vascular endothelial cells present a rich source of inflammation mediating compounds which include histamine, prostaglandins, leukotrienes, neutral proteases, cytokines, bradykinin and nitric oxide. It is postulated that in response to stimulus, substance P may be released from nerve cells and then bind to inflammation mediating cells subsequently triggering release of these and/or other compounds resulting in inflammation. This inflammation is thought to produce pain which includes fibromyalgia pain, migraine headache, arthritis pain, interstitial cystitis pain, myofascial pain syndrome and irritable bowel pain.

What is needed are methods to stop or reduce the occurrence of inflammation and inflammation related pain which occurs in response to neural stimulus.

*Botulinum* Toxin

The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A ("BoNT/A") is the most lethal natural biological agent known to man. About 50 picograms of *botulinum* toxin (purified neurotoxin complex) serotype A is a $LD_{50}$ in mice. One unit (U) of *botulinum* toxin is defined as the $LD_{50}$ upon intraperitoneal injection into female Swiss Webster mice weighing 18–20 grams each. Seven immunologically distinct *botulinum* neurotoxins have been characterized, these being respectively *botulinum* neurotoxin serotypes A, B, $C_1$, D, E, F and G each of which is distinguished by neutralization with serotype-specific antibodies. The different serotypes of *botulinum* toxin vary in the animal species that they affect and in the severity and duration of the paralysis they evoke. For example, it has been determined that BoNt/A is 500 times more potent, as measured by the rate of paralysis produced in the rat, than is *botulinum* toxin serotype B (BoNT/B). Additionally, *botulinum* toxin type B ("BoNt/B") has been determined to be non-toxic in primates at a dose of 480 U/kg which is about 12 times the primate $LD_{50}$ for BoNt/A. *Botulinum* toxin apparently binds with high affinity to cholinergic motor neurons, is translocated into the neuron and blocks the release of acetylcholine.

*Botulinum* toxins have been used in clinical settings for the treatment of neuromuscular disorders characterized by hyperactive skeletal muscles. *Botulinum* toxins, and modified *botulinum* toxins, are also useful for the treatment of pain, see for example, U.S. Pat. Nos. 6,113,915; 6,333,037; 6,235,289; 5,714,468 and; WO 94/15629 each of which is incorporated in its entirety herein by reference.

BoNt/A has been approved by the U.S. Food and Drug Administration for the treatment of blepharospasm, strabismus, hemifacial spasm and cervical dystonia. Additionally a *botulinum* toxin type B has been approved by the FDA for the treatment of cervical dystonia. Non-serotype A *botulinum* toxin serotypes apparently have a lower potency and/or a shorter duration of activity as compared to BoNt/A. Clinical effects of peripheral intramuscular BoNt/A are usually seen within one week of injection. The typical duration of symptomatic relief from a single intramuscular injection of BoNt/A averages about three months.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* serotypes A and E both cleave the 25 kiloDalton (kD) synaptosomal associated protein (SNAP-25), but they target different amino acid sequences within this protein. BoNT/B, D, F and G act on vesicle-associated protein (VAMP, also called synaptobrevin), with each serotype cleaving the protein at a different site. Finally, *botulinum* toxin serotype $C_1$ (BoNT/$C_1$) has been shown to cleave both syntaxin and SNAP-25. These differences in mechanism of action may affect the relative potency and/or duration of action of the various *botulinum* toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the H chain and a cell surface receptor; the receptor is thought to be different for each serotype of *botulinum* toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of *botulinum* toxin activity appears to involve reduction of the disulfide bond joining the H and L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin, B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the *botulinum* toxin protein molecule, for all seven of the known *botulinum* toxin serotypes, is about 150 kD. Interestingly, the *botulinum* toxins are released by *Clostridial bacterium* as complexes comprising the 150 kD *botulinum* toxin protein molecule along with associated non-toxin proteins. Thus, the BoNt/A complex can be produced by *Clostridial bacterium* as 900 kD, 500 kD and 300 kD forms. BoNT/B and $C_1$ are apparently produced as only a 500 kD complex. BoNT/D is produced as both 300 kD and 500 kD complexes. Finally, BoNT/E and F are produced as only approximately 300 kD complexes. The complexes (i.e. molecular weight greater than about 150 kD) are believed to contain a non-toxin hemagglutinin protein and a non-toxin and non-toxic non-hemagglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

BoNt/A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the BoNt/B serotype only cleave a portion of the toxin produced. The exact proportion of nicked to unnicked molecules depends on the length of incubation and the temperature of the culture. Therefore, a certain percentage of any preparation of, for example, the BoNt/B toxin is likely to be inactive, possibly accounting for the known significantly lower potency of BoNt/B as compared to BoNt/A. The presence of inactive *botulinum* toxin molecules in a clinical preparation will contribute to the overall protein load of the preparation, which has been linked to increased antigenicity, without contributing to its clinical efficacy. Additionally, it is known that BoNt/B has, upon intramuscular injection, a shorter duration of activity and is also less potent than BoNt/A at the same dose level.

It has been reported (as exemplary examples) that BoNt/A has been used clinically as follows:

(1) about 75–125 units of BOTOX®[1] per intramuscular injection (multiple muscles) to treat cervical dystonia;

[1] Available from Allergan, Inc., of Irvine, Calif. under the tradename BOTOX®.

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
  (a) flexor digitorum profundus: 7.5 U to 30 U
  (b) flexor digitorum sublimus: 7.5 U to 30 U
  (c) flexor carpi ulnaris: 10 U to 40 U
  (d) flexor carpi radialis: 15 U to 60 U
  (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

The tetanus neurotoxin acts mainly in the central nervous system, while *botulinum* neurotoxin acts at the neuromuscular junction; both act by inhibiting acetylcholine release from the axon of the affected neuron into the synapse, resulting in paralysis. The effect of intoxication on the affected neuron is long lasting and until recently has been thought to be irreversible. The tetanus neurotoxin is known to exist in one immunologically distinct serotype.

SUMMARY

The present invention provides for methods to treat various types of inflammation and pain associated with inflammation.

In accordance with the present invention there are provided methods for treating neurogenic inflammation and neurogenic inflammation pain. The methods may include administering an effective amount of a composition which includes a *botulinum* toxin component and a substance P component to a patient thereby treating the neurogenic inflammation and/or neurogenic inflammation pain.

The *botulinum* toxin component may include an $H_N$ and an L chain. For example, the $H_N$ may be obtained from a *botulinum* toxin serotype A, serotype B, serotype C, serotype D, serotype E, serotype F or serotype G. Also for example, the L chain may be obtained from a *botulinum* toxin serotype A, serotype B, serotype C, serotype D, serotype E, serotype F or serotype G.

In accordance with the invention the substance P component may be a substance P, a precursor of substance P or a substance P analogue.

The present invention provides for methods for treating pain caused by inflammation including fibromyalgia pain, myofascial pain syndrome pain, arthritis pain, migraine headache pain, irritable bowel syndrome pain, Crohn's disease pain and interstitial cystitis pain.

In accordance with the present invention, the compositions may be administered subcutaneously, intramuscularly or systemically. The compositions may be administered with a needle, by needleless injection orally, by inhalable delivery methods such as an inhalable mist or like methods.

Methods of the present invention provide for pain relief ranging from about 5% to about 100% in effectiveness. For example, pain may be reduced by about 20%, about 40%, about 50%, about 60%, about 80% or about 100%.

The present invention also provides for methods for inhibiting pain caused by degranulation of mast cells and/or release of inflammation mediating compounds from vascular endothelial cells. The method may include administering to a patient an effective amount of a composition which includes a *botulinum* toxin component attached to a substance P component, thereby inhibiting pain caused by degranulation of mast cells and/or release of inflammation mediating compounds from vascular endothelial cells. For example, the present invention provides for methods for inhibiting pain caused by histamine release from mast cells. These methods may include administering to a patient an effective amount of a composition which includes a *botulinum* toxin component attached to a substance P component, thereby inhibiting pain caused by histamine release from mast cells.

Each and every feature described herein, and each and every combination of two or more of such features, is included within the scope of the present invention provided that the features included in such a combination are not mutually inconsistent.

DEFINITIONS

An "agent" is defined as a modified neurotoxin that possesses some or all of the biological activity biological activity of an unmodified neurotoxin. Modified neurotoxins include variants and fragments of neurotoxins. One example of a modified neurotoxin, as disclosed herein, is a portion of a *botulinum* toxin coupled to a substance P molecule.

A "*clostridial* neurotoxin" may refer to an intact toxin for example a *botulinum* toxin, *butyricum* toxin or *tetani* toxin or a fragment or portion of a toxin for example a fragment or portion of a *botulimum* toxin, *butyricum* toxin or *tetani* toxin.

"$H_C$" means a fragment obtained from the H chain of a Clostridial toxin which is equivalent, for example functionally equivalent, to the carboxyl end fragment of the H chain, or the portion corresponding to that fragment in the intact H chain involved in binding to a cell surface or cell surface receptor.

"$H_N$" means a fragment or variant obtained from an H chain of a Clostridial toxin which may be functionally equivalent to the portion of an intact H chain involved in the translocation of at least the L chain across an intracellular endosomal membrane into a cytoplasm of a cell. An $H_N$, may result from an $H_C$ being removed from an H chain. An $H_N$ may also result from an H chain being modified such that its $H_C$ no longer binds to cholinergic cell surfaces.

"Heavy chain" means the heavy chain of a *clostridial* neurotoxin or a fragment or variant of an $H_N$ of a *clostridial* neurotoxin. A heavy chain may have a molecular weight of about 100 kDa and can be referred to as H chain, or as H.

"$LH_N$" means a fragment obtained from a *clostridial* neurotoxin that contains the L chain coupled to an $H_N$. $LH_N$ can be obtained from the intact *clostridial* neurotoxin by proteolysis, so as to remove or to modify the $H_C$ domain.

"Light chain" means the light chain of a *clostridial* neurotoxin or a fragment or variant of a light chain of a *clostridial* neurotoxin. A light chain may have a molecular weight of about 50 kDa, and can be referred to as L chain, L, or as the proteolytic domain (amino acid sequence) of a *clostridial* neurotoxin.

"Linker" means a molecule which couples two or more other molecules or components together.

"Local administration" means direct administration by a non-systemic route at or in the vicinity of the site of an affliction, disorder, or perceived pain.

"Neurogenic" means arising from the nervous system. For example, neurogenic inflammation refers to inflammation that may be caused, at least in part, directly or indirectly, by the nervous system.

"Spacer" means a molecule or set of molecules which physically separate and add distance between the components. One function of a spacer may be to prevent steric hindrance between the components.

"Substantial or Substantially" means largely but not entirely. For example, substantial relief of pain may mean pain relief of 10%, 20%, 30%, 40% 50% or more.

"Targeting moiety" means a molecule that has a specific binding affinity for a cell surface or cell surface receptor.

"Variable region" means the part of an antibody that varies extensively from one antibody to another as a result of alternative subunit sequences.

"Variant" means a molecule or peptide which is substantially the same as that of a disclosed molecule or peptide in its structure and function. For example, a variant of a specified light chain may have non-consequential amino acid sequence substitutions when compared to the amino acid sequence of the specified light chain. Variants may be considered to be equivalent to the specifically disclosed molecules and as such are within the scope of the invention.

DESCRIPTION

This invention is based upon the discovery that inflammation pain can be treated by administering to a patient an agent which includes a clostridial neurotoxin component and a targeting moiety component, wherein the targeting moiety component may bind to cells involved in mediating inflammation.

The mechanism of action for these agents in alleviating pain is currently not fully understood. However, without wishing to limit the invention to any particular theory or mechanism of operation, it is believed that the agents disclosed herein may target cells, for example, mast cells and/or vascular endothelial cells which may have receptors for the targeting moieties, for example, a substance P targeting moiety.

Mast cells and vascular endothelial cells present many distinct biologically active, inflammation mediators that may include histamine, prostaglandins, leukotrienes, neutral proteases, cytokines bradykinin and nitric oxide. Release of these and/or other mediators may contribute to the events which cause neurogenic inflammation. Further examples of mediators that may contribute to neurogenic inflammation are discussed in First (U.S. Pat. No. 6,063,768) which is incorporated in its entirety herein by reference.

Sensory neurons containing substance P are thought to be involved in regulating the inflammatory and immune response in the peripheral tissues that they innervate. It is theorized that these sensory neurons release substance P which binds to and causes secretion from inflammation mediating cells. For example, substance P may bind to mast cell receptor sites thereafter triggering degranulation which includes secretion from mast cells of histamine, prostiglandins, leukotrines, serotonin and other molecules that may serve as inflammatory mediators (Spanos et al. J of Urology Vol 157 p 669–672; Toyoda et al Arch Dermatol Res Vol 292 p 418–421). In another example, substance P may trigger release of inflammation mediators such as bradykinin, nitric oxide and vasoactive intestinal peptide from vascular endothelial cells.

It is theorized that inflammatory mediator release triggered by substance P begins with the initial binding of substance P to specific receptors which may be mobile and randomly distributed on the membrane surface of certain cells, for example, mast cells and/or vascular endothelial cells. These substance P-receptor complexes may accumulate in specialized regions of the membrane termed coated pits. From this stage, receptor mediated endocytosis (RME) may proceed to the formation of smooth-walled vesicles which allow entry of the substance P-receptor complexes into the cell. These vesicles, often referred to as "endosomes" or "receptosomes," may fuse together or combine to produce larger vesicles. Subsequently, the internal pH of the endosomes may be decreased by the action of proton pumps. This decrease in pH may change the conformation of the receptor and/or substance P resulting in the release of the substance P from the receptor and the formation of separate receptor-containing vesicles and substance P-containing containing vesicles. The resulting substance P vesicles along with the internalized substance P, may be delivered to and fused with lysosomes where the eventual breakdown of the vesicles and release of the substance P likely takes place.

It is thought that at some point after formation of the substance P-receptor complex, possibly after internalization of the complex, release of inflammation mediators is triggered.

During secretion or exocytosis, the mediators may be included in vesicles which fuse to the inner surface of the cell membrane thereby releasing the vesicle contents to the outside of the cell. Without wishing to limit the present invention to any theory or mechanism of operation, it is theorized that interference with the exocytosis process may be the mode of action of the agents of the present invention.

It is theorized that agents of the present invention may operate by first targeting inflammation mediating cells by use of a targeting moiety component such as substance P, and then prevent or reduce the secretion of inflammation producing molecules by cleaving or by otherwise interfering with the function of proteins involved in the secretory process by use of a light chain component, for example, a botulinum light chain component. A heavy chain component, for example $H_N$, may also function in certain embodiments of the present invention by, for example, assisting in the release of an agent of the invention from intracellular vesicles, for example, endosomes.

The agents described for use in this invention may be very specific for treating inflammation pain without being cytotoxic because they may not substantially or significantly interact with and/or interfere with neurons. Also, the agents can alleviate pain without being cytotoxic to their target neurons. Because of lack of neural interaction and lack of cytotoxicity, agents within the scope of the present invention can be administered either locally at or near sites of inflammation or inflammation pain or systemically.

Agents may be used to treat conditions cause by inflammation, for example neurogenic inflammation. Examples of conditions caused by neurogenic inflammation that may be treated by methods of the present invention include pain associated with fibromyalgia, certain forms of arthritis, myofascial pain syndrome, interstitial cystitis and irritable bowel syndrome. Additional examples of conditions that may be treated in accordance with the present invention include myasthenia gravis, systemic lupus erythematosus, discoid lupus erythematosus, organ transplant, tissue transplant, fluid transplant, Graves disease, thyrotoxicosis, autoimmune diabetes, haemolytic anaemia, thrombocytopenic purpura, neutropenia, chronic autoimmune hepatitis, autoimmune gastritis, pernicious anaemia, Hashimoto's thyroiditis, Addison's disease, Sjogren's syndrome, primary biliary cirrhosis, polymyositis, scleroderma, systemic sclerosis, pemphigus vulgaris, bullous pemphigoid, myocarditis, rheumatic carditis, glomerulonephritis, uveitis, orchitis, ulcerative colitis, vasculitis, atrophic gastritis, pernicious anaemia, type 1 diabetes mellitus. Further examples of conditions that may be caused by neurogenic inflammation that may be treated by methods of the present invention are discussed in First (U.S. Pat. No. 6,063,768).

According to one broad aspect of the invention, methods are provided for the use of a clostridial neurotoxin component covalently coupled to a targeting moiety. The clostridial neurotoxin component may be obtained from *Clostridium beratti*, *Clostridium butyricum*, or *Clostridium botulinum*, for example, *Clostridium botulinum* toxin types A, B, C, D, E, F and G may be used.

The clostridial neurotoxin component may include only a fragment of the entire neurotoxin. For example, it is known in the art that the $H_c$ of the neurotoxin molecule can be removed from the other segment of the H chain, the $H_N$, such that the $H_N$ fragment remains disulphide linked to the L chain of the neurotoxin molecule to provide a fragment known as the $LH_N$. In addition, $LH_N$ can be produced by modifying the $H_c$ fragment to reduce or eliminate the targeting affinity or ability of $H_C$ to bind to its native target site. $H_C$ can be modified by methods known in the art, for example, alterations to the amino acid sequence of the $H_c$ or chemical modification to the $H_c$. Furthermore, the light chain or a fragment of the light chain, with no associated H chain or H chain fragment, can be coupled to a targeting moiety in accordance with the present invention. Therefore, in one embodiment of the present invention $LH_N$ of a clostridial neurotoxin is covalently coupled to a targeting moiety, for example, substance P. In another embodiment, the L chain of a clostridial neurotoxin is covalently coupled to a targeting moiety, for example, substance P.

In another embodiment, the agent includes an H chain of a clostridial neurotoxin, in which the $H_c$ is removed, mutated or chemically modified to reduce or eliminate the ability of $H_c$ to bind to the neurotoxin receptors at the neuromuscular junction combined with the L-chain of a different clostridial neurotoxin, to form a hybrid. For example, in one embodiment, the clostridial neurotoxin component comprises an H chain with the $H_c$ removed, mutated or chemically modified obtained from *botulinum* toxin type A, and an L chain obtained from another *botulinum* toxin type. The described hybrid is covalently coupled to a targeting moiety.

In another embodiment, the agent includes an L chain of a clostridial neurotoxin, or a fragment of the L chain containing the endopeptidase activity, linked to a targeting moiety.

In a broad embodiment, spacers may be used to physically separate components of agents used in accordance with the present invention. For example, an agent of the present invention may comprise an L chain or a $LH_N$ connected to a targeting moiety, for example substance P, through a spacer. A spacer may function to create a distance between the components to minimize or eliminate steric hindrance of the components that may otherwise occur.

In one embodiment, the spacer region is made up of sugar molecules, for example, saccharides, glucose, etc. In another embodiment, the spacer region may be constructed from an aliphatic chain. In another embodiment, the spacer regions may be constructed by linking together a series of amino acids, preferably glycine because glycine are small and are devoid of any functional group. In yet another embodiment, the spacer region may comprise one or more of the sugar molecules, aliphatic chains, and amino acids.

In one embodiment, a spacer comprises a proline, serine, threonine and/or cysteine-rich amino acid sequence similar or identical to an immunoglobulin hinge region. For example, the spacer may comprise the amino acid sequence of a human immunoglobulin g1 hinge region.

Spacers may comprise hydrocarbon moieties, for example, hydrocarbon moieties represented by the chemical formulas:

$HOOC-(CH_2)_n-COOH$, where $n=1-12$ or, $HO-(CH_2)_n-COOH$, where $n>10$

In one embodiment, linkers may be used to link together two or more molecules, components and/or spacers. For example, a Linker may be used to link a targeting moiety to a L or $LH_N$. In another embodiment, a Linker (Y) may be employed to link an L or $LH_N$ to a spacer; in turn, that spacer may then be linked to targeting moiety by another Linker (Y), forming, for example, an agent comprising the structure:

L-Y-spacer-Y-Targeting Moiety.

Examples of substances that can be used as linker (Y) are 2-iminothiolane, N-succinimidyl-3-(2-pyridyldithio)propionate (SPDP), 4-succinimidyloxycarbonyl-alpha-(2-pyridyldithio)toluene (SMPT), m-maleimidobenzoyl-N-hydroxysuccinimide ester (MBS), N-succinimidyl(4-iodoacetyl)aminobenzoate (SIAB), succinimidyl 4-(p-maleimidophenyl)butyrate (SMPB), 1-ethyl-3-(3-dimethylaminopropyl)carbodiimide (EDC), bis-diazobenzidine and glutaraldehyde.

In one embodiment, a linker may be attached to an amino group, a carboxylic group, a sulfhydryl group or a hydroxyl group or an amino group of a component. For example, a linker may be linked to a carboxyl acid group of an amino acid of a targeting moiety.

Although the described chemistry may be used to couple components of agents used in the invention, any other coupling chemistry known to those skilled in the art capable of chemically attaching one component to another component of an agent of the invention is included within the scope of the present invention.

In one embodiment, an agent comprises an $H_N$ and/or an L chain and a targeting moiety, covalently linked together. For example, the $H_N$ may be linked to the L chain and the L chain may be linked to the targeting moiety. In another example, the $H_N$ may be linked to the targeting moiety and to the L chain. In still another example, the targeting moiety may be linked to $H_N$ and the L chain. In still another example, the L chain may be linked to the H, and the targeting moiety. Linkers and/or spacers may be used between some, all or none of the components in these examples.

In another embodiment, the targeting moieties may be components that are substantially similar to substance P. These components include substance P precursors, fragments and analogs. The history, isolation, identification, and synthesis of substance P and its precursors, fragments and analogs are disclosed in U.S. Pat. No. 5,891,842 (incorporated herein by reference in its entirety).

Substance P is an 11 amino acid peptide which has a number of different natural and synthetic precursor forms; has been demonstrated to be converted into a variety of naturally occurring amino-terminal peptide fragments; and can be obtained in analog format compromising, substituted counterparts thereof, for example, lysine methyl ester, D-amino acids or disulfide bridges substitutions, which may thereby yield more stable and discriminating formulations. A representative listing of substance P and its related chemical entities is provided by Table I below. The amino acid sequence (1) in Table I (Arg-Pro-Lys-Pro-Gln-Gln-Phe-Phe-Gly-Leu-Met-amide) can be referred to as SEQ ID NO: 1, and the subsequent 17 amino acid sequences set forth in Table one can be similarly identified as SEQ ID NO:2 to SEQ ID NO:18.

TABLE 1

Substance P, and Representative Precursors, Fragments and Stabilized Or Substituted Analogs

| | Name | Formula |
|---|---|---|
| (1) | Substance P | Arg-Pro-Lys-Pro-Gln-Gln-Phe-Phe-Gly-Leu-Met-amide |

Natural Precursors:

| | Name | Formula |
|---|---|---|
| (2) | Substance P-Glycine* | Arg-Pro-Lys-Pro-Gln-Gln-Phe-Phe-Gly-Leu-Met-Gly |
| (3) | Substance P-Glycine-Lysine* | Arg-Pro-Lys-Pro-Gln-Gln-Phe-Phe-Gly-Leu-Met-Gly-Lys |

TABLE 1-continued

Substance P, and Representative Precursors,
Fragments and Stabilized Or Substituted Analogs

| Name | Formula |
|---|---|
| (4) Substance P-Glycine-Lysine Arginine* | Arg-Pro-Lys-Pro-Gln-Gln-Phe-Phe-Gly-Leu-Met-Gly-Lys-Arg |

Carboxy-Ester Synthetic Precursors:

| | | |
|---|---|---|
| (5) | Substance P-Glycine Methyl Ester° | Arg-Pro-Lys-Pro-Gln-Gln-Phe-Phe-Gly-Leu-Met-Gly-OMe |
| (6) | Substance P-Glycine-Lysine Methyl Ester° | Arg-Pro-Lys-Pro-Gln-Gln-Phe-Phe-Gly-Leu-Met-Gly-Lys-OMe |
| (7) | Substance P-Glycine-Lysine Arginine Methyl Ester° | Arg-Pro-Lys-Pro-Gln-Gln-Phe-Phe-Gly-Leu-Met-Gly-Lys-Arg-OMe |
| (8) | Substance P-Glycine Ethyl Ester° | Arg-Pro-Lys-Pro-Gln-Gln-Phe-Phe-Gly-Leu-Met-Gly-OEth |
| (9) | Substance P-Glycine-Lysine Ethyl Ester° | Arg-Pro-Lys-Pro-Gln-Gln-Phe-Phe-Gly-Leu-Met-Gly-Lys-OEth |
| (10) | Substance P-Glycine-Lysine Arginine Ethyl Ester° | Arg-Pro-Lys-Pro-Gln-Gln-Phe-Phe-Gly-Leu-Met-Gly-Lys-Arg-OEth |

Naturally-Occurring Amino-Terminal Peptide Fragments:

| | | |
|---|---|---|
| (11) | Substance P/1-4# | Arg-Pro-Lys-Pro |
| (12) | Substance P/1-7# | Arg-Pro-Lys-Pro-Gln-Gln-Phe |
| (13) | Substance P/1-9# | Arg-Pro-Lys-Pro-Gln-Gln-Phe-Phe-Gly |

Analogs Comprising Synthetic D-Amino Acids
Or Disulfide (Cys—Cys) Bridges:

| | | |
|---|---|---|
| (14) | [D-Pro2, D-Phe7, D-Trp9]-Substance P¢ | Arg-D-Pro-Lys-Pro-Gln-Gln-D-Phe-Phe-D-Trp-Leu-Met-amide |
| (15) | [D-Pro2, D-Phe7, D-Trp9]-(Substance P-Glycine¢) | Arg-D-Pro-Lys-Pro-Gln-Gln-D-Phe-Phe-D-Trp-Leu-Met-Gly |
| (16) | [D-Pro2, D-Trp7, D-Trp9]-Substance P¢ | Arg-D-Pro-Lys-Pro-Gln-Gln-D-Trp-Phe-D-Trp-Leu-Met-amide |
| (17) | [D-Pro2,D-Trp7, D-Trp9]-Substance P-Glycine¢ | Arg-D-Pro-Lys-Pro-Gln-Gln-D-Trp-Phe-D-Trp-Leu-Met-Gly |
| (18) | [Cys3, Cys6, Tyr8, Pro10]-Substance P¢ | Arg-Pro-Cys-Pro-Gln-Cys-Phe-Tyr-Gly-Pro-Met-amide |

*Shimonka et al., J. Neurochem. 59:81–92 (1992)
°Lee et al., Eur. J. Biochem. 114:315–327 (1981); Pernow, B., Pharmacol. Rev. 35:86–138 (1983); and Regoli et al., TIPS 9:290–295 (1988).
Stewart et al., Nature 262:784–785 (1986); and Skilling et al., J. Neurosci. 10:1309–1318 (1990)¢Lavielle et al., Biochem. Pharmacol. 37:41 (1988); and Quirion, R. and T. V. Dam, Regulatory Peptides 22:18 (1988)

In one embodiment, agents for use in accordance with the invention comprise a hybrid of two clostridial neurotoxins. For example, the H chain, in one embodiment $H_N$, may be obtained from *botulinum* toxin A, B, C, D, E, F or G and the L chain obtained from another *botulinum* toxin selected from *botulinum* toxin A, B, C, D, E, F or G. The two chains from different *botulinum* toxin serotypes may be joined together by covalent bonds and/or by disulfide bonds and/or by hydrogen bonds and/or by ionic bonds to for a hybrid $LH_N$. This hybrid $LH_N$, may be linked to a targeting moiety, for example, substance P or a component that is substantially similar to substance P, for example, substance P precursors, substance P analogs and substance P fragments, by standard methodologies known in the art. In one embodiment the targeting moiety is covalently linked to a hybrid $LH_N$.

In another embodiment, the agents comprises an L chain of a *clostridial* neurotoxin, or a fragment of an L chain containing the endopeptidase activity, coupled to substance P or component that is substantially similar to substance P. The L chain or fragment of the L chain is obtained from *botulinum* toxin A, B, C, D, E or G and is coupled to substance P or components that are substantially similar to substance P, for example, substance P precursors, substance P analogs and substance P fragments, by standard methodologies known in the art. Linkers and/or spacer components may be used in the coupling.

An agent used in accordance with the present invention may comprise a heavy chain or a portion of a heavy chain of a *clostridial* neurotoxin. Even more preferably, the $H_N$ of the heavy chain is able to facilitate the transfer of the agent across an endosome membrane into the cytosol of a cell, for example, a mast cell. The *clostridial* neurotoxin heavy chain may be obtained from *Clostridium botulinum* neurotoxin type A. In other embodiments, the heavy chain may be obtained from *Clostridium botulinum* types B, C, D, E, F, G and mixtures thereof. Also, the heavy chain may be obtained from neurotoxins obtained from *Clostridium baratii* and *Clostridium butyricum* or *Clostridium tetani*.

Agents that may be used in accordance with the present invention are also disclosed in U.S. patent application Ser. Nos. 09/489,667, 09/922,093 and 09/625,098 which are incorporated in their entirety herein by reference.

According to another broad aspect of this invention, recombinant DNA methodologies may be used to produce the components of agents useful in accordance with the invention, including the targeting moiety, the light chain or light chain fragment and/or the heavy chain or heavy chain fragment. These techniques may include steps of obtaining cloned genes from natural sources, or from synthetic oligonucleotide sequences, which may encode clostridial neurotoxin components including *clostridial* neurotoxin heavy chains, light chains or variants thereof, modified *clostridial* neurotoxin chains and/or fragments of the chains. Cloned genes may also encode a targeting moiety.

The genes may be cloned into, for example, cloning vectors, such as phages or plasmids or phagemids. The recombinant vectors are transformed into host cells, for example, into a prokaryotic cell, for example, *E. coli*. Proteins can be expressed and then isolated using conventional techniques.

Fusion genes may be used which encode more than one component of an agent. For example, a targeting moiety and a *botulinum* toxin heavy chain and/or light chain and/or a fragment of a heavy and/or a fragment of a light chain, can be produced from a single cloned gene as a fusion protein. Alternatively, individual components obtained from recombinant techniques can be chemically coupled to other components obtain from other sources. For example, a synthetic or naturally occurring targeting moiety component may be coupled to a recombinant L chain or to a recombinant fusion $LH_N$. The linkages between the *clostridial* components and the targeting moieties may include appropriate spacer components which may also be DNA encoded and included in the fusion gene construct.

In another embodiment, the required $LH_N$, which may be a hybrid of an L chain and an $H_N$ from different *clostridial* toxin types, is expressed recombinantly as a fusion protein. Such $LH_N$ hybrid may also be coupled to the targeting moiety, which may further include one or more spacer regions between them.

In another embodiment of the invention the L chain of a *clostridial* neurotoxin, or a fragment of the L chain containing the endopeptidase activity, is expressed recombinantly as a fusion protein with the $H_N$ of the H chain and the targeting moiety. The expressed fusion protein may also include one or more spacer regions. For example, the L chain may be fused to $H_N$ which is in turn fused to the targeting moiety. In another example, the $H_N$ may be fused to the L chain which is in turn fused to the targeting moiety. Spacer components may be expressed recombinantly between some or all of the components of an agent of the invention.

In one embodiment of producing a hybrid of $LH_N$, the L chain is obtained from *botulinum* toxin type B and the amine end segment of the $H_N$ chain fragment is obtained from *botulinum* toxin type A. The $H_N$ fragment of the *botulinum* toxin type A is produced according to the method described by Shone C. C., Hambleton, P., and Melling, J. (1987, Eur. J. Biochem. 167, 175–180) and the L chain of *botulinum* toxin type B according to the method of Sathyamoorthy, V. and DasGupta, B. R. (1985, J. Biol. Chem. 260, 10461–10466). The free cysteine on the amine end segment of the H chain fragment of *botulinum* toxin type A is then derivatized by the addition of a ten-fold molar excess of dipyridyl disulphide followed by incubation at 4 degrees C. overnight. The excess dipvridyl disulphide and the thiopyridone by product are then removed by desalting the protein over a PD10 column (Pharmacia) into PBS.

The derivatized $H_N$ is then concentrated to a protein concentration in excess of 1 mg/ml before being mixed with an equimolar portion of L chain from *botulinum* toxin type B (>1 mg/ml in PBS). After overnight incubation at room temperature the mixture is separated by size exclusion chromatography over Superose 6 (Pharmacia), and the fractions analyzed by SDS-PAGE. The chimeric $LH_N$ is then available to produce a conjugated agent which includes a targeting moiety component.

The example described above is purely illustrative of the invention. In synthesizing the agents, the coupling of the targeting moieties to the clostridial components, for example the modified clostridial neurotoxins or fragments thereof, may be achieved via chemical coupling using reagents and techniques known to those skilled in the art. Thus, any coupling chemistry capable of covalently attaching the targeting moieties of the agents to clostridial neurotoxin components and known to those skilled in the art is covered by the scope of this application.

In one embodiment of the invention, there are provided methods for the treatment of pain which comprise locally administering directly to a region of inflammation and/or inflammation pain in a patient, in therapeutically effective doses, an agent of the invention. In another embodiment, the invention provides for administration of an agent of the invention near the site of inflammation and/or inflammation pain in a patient, for example, within about 0.1 to about 100 cm, or for example, about 1 cm to about 10 cm from the site of inflammation and/or inflammation pain.

Known local drug administration methods suitable for administration may be used including injection, with or without the use of a needle, and by insertion of a controlled release implant. Routes of administration include, without limitation, transdermal, peritoneal, subcutaneous, intramuscular, and intrarectal injection.

In another embodiment, a therapeutically effective dose of an agent of the invention is administered by systemic administration, for example, oral administration, intravenous administration or administration as an inhalant.

An agent, such as botulinum toxin component-substance P or components that are substantially similar to substance P can require, according to the methods of the present invention, from about 1 to 7 days to begin to achieve an effect upon a site of inflammation pain.

The amount of the agents administered can vary widely according to the particular disorder being treated, its severity and other various patient variables including size, weight, age, and responsiveness to therapy.

Methods of the present invention provide for pain relief ranging from about 56 to about 100% in effectiveness. For example, pain may be reduced by about 20%, about 40%, about 50%, about 60%, about 80% or about 100%.

Methods for determining the appropriate route of administration and dosage are generally determined on a case-by-case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill).

Generally, the dose of an agent to be administered will vary with the age, presenting condition and weight of the patient to be treated. The potency of the agent will also be considered. Agent (e.g. conjugate) potency is expressed as a multiple of the $LD_{50}$ value of an agent of the invention for a mouse. A "U" or "unit" of an agent can be defined as the amount of toxin that kills 50% of a group of mice that were disease-free prior to inoculation with the agent. Alternatively, potency may be expressed as the $LD_{50}$ value of an agent that would be produced by an equal molar amount of botulinum toxin with a functional $H_C$.

Agents of the invention can be administered in a dose of about 0.01 units up to about 1,000 units. In one embodiment, individual dosages of about 1 unit to about 30 units are used. In another embodiment, individual dosages of about 30 units to about 60 units are used. In still another embodiment, individual dosages of about 60 units to about 180 units are used. Generally, the agents may be administered as a composition at a dosage that is proportionally equivalent to, for example, about 2.5 cc/100 units. Those of ordinary skill in the art will know, or can readily ascertain, how to adjust these dosages for an agent of greater or lesser potency.

Preferably, the lowest therapeutically effective dosage will be administered to the patient. The lowest therapeutic dosage is that dosage which results in detection by the patient of a reduction in the occurrence and/or magnitude of pain experienced by the patient, for example, pain experience by a patient which is associated with neurogenic inflammation.

Methods for assessing or quantifying the amount of pain experienced by a patient are well known to those skilled in the art. For example, a patient can be given a pain assessment test in which the patient quantifies the degree of pain based on a scale. One example would be assigning the patient's pain a number based on a scale of 1 to 10, where a "10" would indicate the worst degree of pain the patient might imagine. A pain measure of 4 from an original pain score of 8 would be a 50% reduction in pain. Thus, the amount of conjugate required to achieve that 50% reduction in pain could be considered 1 U of the clostridial toxin component-targeting moiety conjugate. Alternatively, the patient's pain may be measured as the duration of pain. One unit of the conjugate of the invention would accordingly reduce the duration of pain by 50%. In addition, a number of physiological measures, such as heart rate, respiratory rate, blood pressure, and diaphoresis, may be used alone or together with the methods described above, to quantify the amount of the patient's pain.

In an initial treatment, a low dosage may be administered at one site to determine the patient's sensitivity to, and tolerance of, the agent. Additional administration of the same or different dosages may be performed as necessary.

In one embodiment, an agent of the invention is administered intramuscularly. However, for some indications, extramuscular injection may be the most efficacious route of administration. Such injection may, for example, be made subcutaneously or, preferably, perivascularly (to produce infiltration of the agent into innervated tissue). In one embodiment, the site for injection of the agent is in or near the extramuscular regions.

The agents may be administered by, for example, injection using a needle or by needleless injection. The injections may be repeated as necessary.

In needleless injection delivery methods, microprojectile drug particles may be coated with an agent and then discharged into the skin from an external delivery device. Depending on the discharge velocity and the distance from the injection site, the drug particles penetrate through the stratum corneum to different layers of the epidermis, dermis and underlying muscle. As the microprojectiles penetrate through epidermal and dermal cells, or are deposited in these cells, the agent is released. Individual layers of skin cells or underlying muscle cells may be targeted for the microprojectiles.

A range for administration of an agent, such as a $LH_N$-substance p conjugate (or targeting moiety substantially similar to substance P including substance P precursors, fragments and analogs), so as to achieve an antinociceptive effect in the patient treated may be from about $10^{-2}$ U/kg to about 100 U/kg, for example between about $10^{-1}$ U/kg to about 10 U/kg. Dosage for a particular agent may depend on factors such as the condition to be treated and the method of administration. An appropriate dosage in a given circumstance may readily be determined by a physician of ordinary skill.

A range for administration of an agent, such as an a L chain-substance P conjugate, (or targeting moiety substantially similar to substance P including substance P precursors, fragments and analogs) so as to achieve an antinociceptive effect in the patient treated may be from about $10^{-2}$ U/kg to about 100 U/kg, for example between about $10^{-1}$ U/kg to about 10 U/kg. Dosage for a particular agent may depend on factors such as the condition to be treated and the method of administration. An appropriate dosage in a given circumstance may readily be determined by a physician of ordinary skill.

Dosage for a particular agent may depend on factors such as the condition to be treated and the method of administration. A physician of ordinary skill may readily determine an appropriate dosage in a given circumstance.

The invention having been fully described, examples illustrating its practice are set forth below. These examples should not, however, be considered to limit the scope of the invention, which is defined by the appended claims.

EXAMPLES

Example 1

Methods for Determining Potency of Botulinum Toxin Component-Targeting Moiety Conjugates The traditional unit of measure for *botulinum* toxin potency is the mouse $LD_{50}$ unit. That is, one unit (1 U) of *botulinum* toxin is the amount that kills 50% of a group of 18–20 gram female Swiss-Webster mice.

The unit of measure for potency of a *botulinum* toxin component-targeting moiety conjugate may also be determined by $LD_{50}$ assays. In particular, 1 U of the *botulinum* toxin component-targeting moiety component conjugate (for example, a $LH_N$-substance P conjugate) is the amount of the conjugate that kills 50% of a group of 18–20 gram female Swiss-Webster mice.

Alternatively, potency of *botulinum* toxin component-targeting moiety component conjugate may be determined by the amount of pain reduction in a patient induced by a measured amount of conjugate. For example, the pain reduction in a patient may be estimated to be 50% upon injection of a measured amount of a conjugate into a site of inflammation. Thus, the potency can be measured as the amount of conjugate that reduces a patient's pain by 50%.

Methods for assessing or quantifying the amount of pain experienced by a subject are well known to those skilled in the art. For example, a subject can be given a pain assessment test in which the subject quantifies the degree of pain based on a scale. One example would be assigning the subject's pain a number based on a scale of 1 to 10, where a "10" would indicate the worst degree of pain the subject might imagine. A pain measure of 4 from an original pain score of 8 would be a 50% reduction in pain. Thus, the amount of conjugate required to achieve that 50% reduction in pain could be considered 1 U of the *botulinum* toxin component-targeting moiety component conjugate. Alternatively, the subject's pain may be measured as the duration of pain. One unit of the conjugate of the invention would accordingly reduce the duration of pain by 50%. In addition, a number of physiological measures, such as heart rate, respiratory rate, blood pressure, and diaphoresis, may be used individually or in combination to quantify a subject's pain. These procedures may also be used in combination with the subjective methods described above, to quantify the amount of the subject's pain.

Example 2

Treatment of Neurogenic Inflammation Pain

A patient, age 45, experiencing acute neurogenic inflammation pain is treated by intravenous administration with between about 0.1 U/kg and about 30 U/kg, (for example, about 4 U), of an agent comprising an $LH_N$ *botulinum* toxin type A-substance P conjugate. Within 1–7 days after agent administration the patient's pain is substantially alleviated. The duration of pain reduction is from about 2 to about 6 months.

Example 3

Treatment of Neurogenic Inflammation Pain

A patient, age 36, experiencing inflammation pain of neurogenic origin is treated by direct administration to the site of pain of between about 0.1 U/kg and about 30 U/kg, (for example, from about 1 U to about 10 U), of an agent comprising a *botulinum* toxin type A L chain-substance P conjugate. A physician of ordinary skill may readily determine the dosage, site of injection, and frequency of administration. Within 1–7 days the pain symptoms are substantially alleviated. The duration of pain reduction is from about 2 to about 6 months.

Example 4

Treatment of Neurogenic Inflammation Pain

A patient, age 45, experiencing acute neurogenic inflammatory pain is treated by administration, for example by injection directly to a site of pain with an amount of an agent comprising *botulinum* toxin type A, B, C, D, E, F and/or G $H_N$ and type A, B, C, D, E, F and/or G L chain-substance P, substance P analog and/or substance P fragment conjugate that reduces pain in the subject by about 50%. A physician of ordinary skill may readily determine the dosage, method of administration, and frequency of administration. Within 1–7 days after agent administration the patient's pain is alleviated by about 50% (in particular, the patient's pain score is originally a 6, and after treatment, the patient scores his pain as a 3). The duration of pain reduction is from about 2 to about 6 months.

Example 5

Treatment of Neurogenic Inflammation Pain

A patient, age 36, experiencing neurogenic inflammation pain (score of 8) is treated by intravenous administration of about 1 U to about 20 U of an agent comprising a *botulinum* toxin type A, B, C, D, E, F and/or G L chain-substance P, substance P analog and/or substance P fragment conjugate that reduces the pain in the subject by about 80% (score of about 1 to about 2). A physician of ordinary skill may readily determine the dosage and frequency of administration. Within 1–7 days the pain symptoms are reduced by about 80%. The duration of pain reduction is from about 2 to about 6 months.

Example 6

Treatment of Fibromyalgia

A 37-year old woman complains of pain "all over," specifically in the occiput, neck, shoulders, lower back, hips, and right leg.

At the time of evaluation, the patient complains specifically of occipital headache, which she describes as burning and aching. She complains of neck pain and stiffness. Aching pain in the upper back and shoulders is constant, as is pain in a band-like fashion across the lower back. She also notes a great increase in her upper back and neck pain. The patient injures her lower back one year prior to this evaluation-while working as a nurse's aide as she transfers a patient. She subsequently continues to experience lower back, hip, and right leg pain and stiffness.

Upon examination, it is found that the patient tests positive for pain sensitivity in 11 of the 18 fibromyalgia tender points. Specifically, tenderness is present in the left and right occiput, the left and right cervical regions, the left and right trapizious, the left and right gluteal, the left and right supraspinatus and the right greater trochanter. A diagnosis of fibromyalgia is made.

The patient is treated by injection of about 1 to about 40 units of *botulinum* toxin type A $LH_N$-substance P conjugate into tendon insertion sites near the perceived sources of pain. Within one week of treatment, the patient notes a substantial decrease in pain felt throughout her body. Pain relief lasts for approximately eight months.

Example 7

Treatment of Myofascial Pain Syndrome

A physical examination reveals a 38-year old woman who suffers nerve damage in an auto accident at the age of 28. She suffers from a steady pain in addition to allodynia in her legs. The patient walks with a normal gait and is able to perform heel walk and toe walk without difficulty. Range of motion of the lumbar and cervical spine is complete. Motor and sensory examination of the upper and lower extremities reveals mild S1 sensory loss on the right side. Reflexes are intact at the knees and ankles.

Radiographics of the cervical and lumbar spine are essentially normal demonstrating only mild degenerative changes.

The patient is diagnosed with myofacial pain syndrome and is treated with injections of about 1 to about 60 units of *botulinum* toxin type A L chain, type B $H_N$ hybrid $LH_N$-substance P conjugate. A physician of ordinary skill may readily determine the dosage, method of administration, and frequency of administration. After approximately 6 days the patient reports herself to be pain free. The relief from pain lasts approximately 6 months at which time the injections are repeated.

Example 8

Treatment of Irritable Bowel

A 30 year old man visits his family physician with chief complaints of persistent pain in the upper and lower back, indigestion, constant tiredness and frequent urination.

The man discloses bouts of gastrointestinal discomfort, both before and after meals. The patient denies any drug use or cigarette smoking, except for an occasional alcoholic drink. Visual observation reveals a man not under distress. Cranial tests are normal. Reflexes are normal. A blood chemistry is ordered. With an exception of a slightly lower K+ level, all other values are normal. Antinuclear antibody, rheumatoid factor, creatine kinase, magnesium, lyme titre, and thyroid function tests are negative. A diagnosis of irritable bowel syndrome is made. The physician prescribes injections of about 1 to about 10 units of *botulinum* toxin type A $LH_N$-substance P conjugate into the wall of the lower small intestine. After one week, the patient reports only mild relief. A further injection is made using about 1 to about 40 units of the same conjugate agent. Pain relief of up to 80% is realized one week after this treatment.

Example 9

Treatment of Migraine Headache

A 34-year-old woman seeks medical attention for migraine headache. The patient reports the symptoms persisting for approximately 5 years. In addition, the patient reports an inability to obtain restful sleep. The patient has been prescribed numerous medications over the years including tylenol III, Propanolol hydrochloride, Dihydroergotamine mesylate, Naratriptan hydrochloride, Sumatriptan succinate and Zolmitriptan. All have met with moderate to little effect.

The patient is intravenously injected with about 1 to about 120 units of a *botulinum* toxin type A L chain, type B $H_N$, $LH_N$-substance P conjugate conjugate.

At 1 week a physical examination reveals no sign of migraine headache pain. Pain relief last for approximately 9 months.

Example 10

Treatment of Arthritis

A patient, age 45, complains of pain in the back and left hip. The patient also reports symptoms of pain and lack of mobility in his left wrist, and in several of his fingers. The patient is diagnosed with rheumatoid arthritis. The patient is treated by an injection of about 1 to about 50 units of a *botulinum* toxin type A L chain, type B $H_N$ hybrid $LH_N$-substance P conjugate and or a *botulinum* toxin type A L chain-substance P conjugate into or near the regions of pain. A physician of ordinary skill may readily determine the specific dosage, site of injection, and frequency of administration. Within 1–7 days after administration the patient's pain is substantially alleviated. The duration of the pain alleviation is from about 1 to about 6 months.

Example 11

Treatment of Interstitial Cystitis

Upon examination, a 56 year old woman complains of chronic pelvic pain, pain with sexual relations, sleep difficulties and incontinence. The patient also reports symptoms of irritable bowel and fatigue. She states that she is suffering from these symptoms for over a year and that just recently the pain is increasing substantially. A diagnosis of interstitial cystitis is made. The patient is treated by injection of about 2 to about 200 units of *botulinum* toxin type A $LH_N$-substance P conjugate into the bladder wall. A physician of ordinary skill may readily determine the specific dosage, site of injection, and frequency of administration. Within 1–7 days after modified neurotoxin administration the patient's pain is substantially alleviated. The duration of the pain alleviation is from about 7 to about 27 months.

Example 12

Treatment of Pain Associated With Fibromyalgia Tender Points

A 36 year old woman has a 15 year history of chronic pain in the upper torso area. Fifteen years prior to evaluation she notes a decrease in mobility in her left elbow and knees. The pain in the left side of her body is thought to be worse than in the right. Upon examination it is revealed that the patient is pain sensitive to firm pressure that is applied sequentially to eight of the eighteen fibromyalgia tender points. In order for a diagnosis of fibromyalgia to be made, 11 of the 18 fibromyalgia tender points must be pain sensitive to application of pressure. Since this standard is not met, the patient is not diagnosed as having fibromyalgia. She is treated with antidepressant medication including amytriptyline (Elavil). The medication has little effect on the level of pain experienced by the patient.

The patient is injected with about 1 to about 20 units of botulinum toxin type A L chain-substance P conjugate into the sites where the patient perceives the pain to originate. A physician of ordinary skill may readily determine the specific dosage, site of injection, and frequency of administration.

Several days after the injections she notes substantial improvement in her pain. This gradually improves over a 2 to 3 week period in which she notes increased mobility in her elbow and knee joints. The patient states that the pain is better than at any time in the last 4 years. The improved condition persists for up to 6 months.

```
                        SEQUENCE LISTING

<160> NUMBER OF SEQ ID NOS: 18

<210> SEQ ID NO 1
<211> LENGTH: 11
<212> TYPE: PRT
<213> ORGANISM: Unknown Organism
<220> FEATURE:
<223> OTHER INFORMATION: Description of Unknown Organism: This fragment
      is a substance P and is very well known in the art.
<220> FEATURE:
<221> NAME/KEY: MOD_RES
<222> LOCATION: (10)
<223> OTHER INFORMATION: Xaa at position 10 is Methionine amide;
<300> PUBLICATION INFORMATION:
<310> PATENT DOCUMENT NUMBER: 5891842
<311> PATENT FILING DATE: 1996-04-12
<312> PUBLICATION DATE: 1999-04-16

<400> SEQUENCE: 1

Arg Pro Lys Pro Gln Gln Phe Phe Gly Leu Xaa
 1               5                  10

<210> SEQ ID NO 2
<211> LENGTH: 12
<212> TYPE: PRT
<213> ORGANISM: Unknown Organism
<220> FEATURE:
<223> OTHER INFORMATION: Description of Unknown Organism: Precursor to
      substance P, which is very well known in the art.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Shimonka, et al.
<303> JOURNAL: J. Neurochem.
<304> VOLUME: 52
<306> PAGES: 81-92
<307> DATE: 1992

<400> SEQUENCE: 2

Arg Pro Lys Pro Gln Gln Phe Phe Gly Leu Met Gly
 1               5                  10

<210> SEQ ID NO 3
<211> LENGTH: 13
<212> TYPE: PRT
<213> ORGANISM: Unknown Organism
<220> FEATURE:
<223> OTHER INFORMATION: Description of Unknown Organism: This fragment
      is a precursor to substance P and is very well known in the art.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Shimonka, et al.
```

-continued

```
<303> JOURNAL: J. Neurochem.
<304> VOLUME: 52
<306> PAGES: 81-92
<307> DATE: 1992

<400> SEQUENCE: 3

Arg Pro Lys Pro Gln Gln Phe Phe Gly Leu Met Gly Lys
 1               5                   10

<210> SEQ ID NO 4
<211> LENGTH: 14
<212> TYPE: PRT
<213> ORGANISM: Unknown Organism
<220> FEATURE:
<223> OTHER INFORMATION: Description of Unknown Organism: This fragment
      is a precursor to substance P and is very well known in the art.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Shimonka, et al.
<303> JOURNAL: J. Neurochem.
<304> VOLUME: 52
<306> PAGES: 81-92
<307> DATE: 1992

<400> SEQUENCE: 4

Arg Pro Lys Pro Gln Gln Phe Phe Gly Leu Met Gly Lys Arg
 1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: This
      fragment is a carboxy-ester synthetic precursor to substance P.
<220> FEATURE:
<221> NAME/KEY: MOD_RES
<222> LOCATION: (12)
<223> OTHER INFORMATION: Xaa at position 12 is Glycine Methyl Ester;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 5

Arg Pro Lys Pro Gln Gln Phe Phe Gly Leu Met Xaa
 1               5                   10

<210> SEQ ID NO 6
<211> LENGTH: 13
<212> TYPE: PRT
<213> ORGANISM: Artificial Sequence
```

```
<220> FEATURE:
<223> OTHER INFORMATION: Description of Artificial Sequence: This is a
      carboxy-ester synyhetic precursor to substance P.
<220> FEATURE:
<221> NAME/KEY: MOD_RES
<222> LOCATION: (13)
<223> OTHER INFORMATION: Xaa at position 13 is Lysine Methyl Ester;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 6

Arg Pro Lys Pro Gln Gln Phe Phe Gly Leu Met Gly Xaa
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: This is a
      carboxy-ester synthetic precursor to substance P.
<220> FEATURE:
<221> NAME/KEY: MOD_RES
<222> LOCATION: (14)
<223> OTHER INFORMATION: Xaa at position 14  is Arginine Methyl Ester;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 7

Arg Pro Lys Pro Gln Gln Phe Phe Gly Leu Met Gly Lys Xaa
 1               5                  10

<210> SEQ ID NO 8
<211> LENGTH: 12
<212> TYPE: PRT
```

```
<213> ORGANISM: Artificial Sequence
<220> FEATURE:
<223> OTHER INFORMATION: Description of Artificial Sequence: This is a
      carboxy-ester synthetic precursor to substance P.
<220> FEATURE:
<221> NAME/KEY: MOD_RES
<222> LOCATION: (12)
<223> OTHER INFORMATION: Xaa at position 12 is Glycine Ethyl Ester;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 8

Arg Pro Lys Pro Gln Gln Phe Phe Gly Leu Met Xaa
  1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: This is a
      carboxy-ester synthetic precursor to substance P.
<220> FEATURE:
<221> NAME/KEY: MOD_RES
<222> LOCATION: (13)
<223> OTHER INFORMATION: Xaa at position 13 is Lysine Ethyl Ester;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 9

Arg Pro Lys Pro Gln Gln Phe Phe Gly Leu Met Gly Xaa
  1               5                  10

<210> SEQ ID NO 10
<211> LENGTH: 14
```

```
<212> TYPE: PRT
<213> ORGANISM: Artificial Sequence
<220> FEATURE:
<223> OTHER INFORMATION: Description of Artificial Sequence: This is a
      carboxy-ester synthetic precursor to substance P.
<220> FEATURE:
<221> NAME/KEY: MOD_RES
<222> LOCATION: (14)
<223> OTHER INFORMATION: Xaa at position 14  is Arginine Ethyl Ester;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lee, et al.
<303> JOURNAL: Eur. J. Biochem.
<304> VOLUME: 114
<306> PAGES: 315-327
<307> DATE: 1981
<300> PUBLICATION INFORMATION:
<301> AUTHORS: Pernow, B.
<303> JOURNAL: Pharmacol. Rev.
<304> VOLUME: 35
<306> PAGES: 86-138
<307> DATE: 1983
<300> PUBLICATION INFORMATION:
<301> AUTHORS: Regoli, et al.
<303> JOURNAL: TIPS
<304> VOLUME: 9
<306> PAGES: 290-295
<307> DATE: 1988

<400> SEQUENCE: 10

Arg Pro Lys Pro Gln Gln Phe Phe Gly Leu Met Gly Lys Xaa
 1               5                  10

<210> SEQ ID NO 11
<211> LENGTH: 4
<212> TYPE: PRT
<213> ORGANISM: Unknown Organism
<220> FEATURE:
<223> OTHER INFORMATION: Description of Unknown Organism: This is a
      naturally occuring amino termal peptide fragment
      derived from substance P.
<220> FEATURE:
<221> NAME/KEY: MOD_RES
<222> LOCATION: (1)..(4)
<223> OTHER INFORMATION: This sequence is made up by the first four
      amino acids of substance P.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<303> JOURNAL: Nature
<304> VOLUME: 262
<306> PAGES: 784-785
<307> DATE: 1986
<300> PUBLICATION INFORMATION:
<303> JOURNAL: J. Neurosci.
<304> VOLUME: 10
<306> PAGES: 1309-1318
<307> DATE: 1990

<400> SEQUENCE: 11

Arg Pro Lys Pro
 1

<210> SEQ ID NO 12
<211> LENGTH: 7
<212> TYPE: PRT
<213> ORGANISM: Unknown Organism
<220> FEATURE:
<223> OTHER INFORMATION: Description of Unknown Organism: This is a
      naturally occuring amino thermal peptide fragment
```

-continued

```
        derived from substance P.
<220> FEATURE:
<221> NAME/KEY: MOD_RES
<222> LOCATION: (1)..(7)
<223> OTHER INFORMATION: This fragment is made up of the first seven
      amino acids of substance P.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<303> JOURNAL: Nature
<304> VOLUME: 262
<306> PAGES: 784-785
<307> DATE: 1986
<300> PUBLICATION INFORMATION:
<303> JOURNAL: J. Neurosci.
<304> VOLUME: 10
<306> PAGES: 1309-1318
<307> DATE: 1990

<400> SEQUENCE: 12

Arg Pro Lys Pro Gln Gln Phe
 1               5

<210> SEQ ID NO 13
<211> LENGTH: 9
<212> TYPE: PRT
<213> ORGANISM: Unknown Organism
<220> FEATURE:
<223> OTHER INFORMATION: Description of Unknown Organism: This is a
      naturally occuring amino thermal peptide fragment
      derived from substance P.
<220> FEATURE:
<221> NAME/KEY: MOD_RES
<222> LOCATION: (1)..(9)
<223> OTHER INFORMATION: This fragment is made of the first nine amino
      acids of substance P.
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<303> JOURNAL: Nature
<304> VOLUME: 262
<306> PAGES: 784-785
<307> DATE: 1986
<300> PUBLICATION INFORMATION:
<303> JOURNAL: J. Neurosci.
<304> VOLUME: 10
<306> PAGES: 1309-1318
<307> DATE: 1990

<400> SEQUENCE: 13

Arg Pro Lys Pro Gln Gln Phe Phe Gly
 1               5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: This is an
      analog of substance P
<220> FEATURE:
<221> NAME/KEY: MOD_RES
<222> LOCATION: (2)
<223> OTHER INFORMATION: Xaa at position 2 is D-form of Proline;
<220> FEATURE:
<221> NAME/KEY: MOD_RES
<222> LOCATION: (7)
<223> OTHER INFORMATION: Xaa in position 7 is D-form of Phenylalanine;
<220> FEATURE:
<221> NAME/KEY: MOD_RES
<222> LOCATION: (9)
```

```
<223> OTHER INFORMATION: Xaa in position 9 is D-form of Tryptophan;
<220> FEATURE:
<221> NAME/KEY: MOD_RES
<222> LOCATION: (11)
<223> OTHER INFORMATION: Xaa in position 11 is Methionine amide;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lavielle, et al.
<303> JOURNAL: Biochem. Pharmacol.
<304> VOLUME: 37
<306> PAGES: 41-
<307> DATE: 1988
<300> PUBLICATION INFORMATION:
<301> AUTHORS: Quirion, R.
       Dam, T.V.
<303> JOURNAL: Regulatory Peptides
<304> VOLUME: 22
<306> PAGES: 18-
<307> DATE: 1988

<400> SEQUENCE: 14

Arg Xaa Lys Pro Gln Gln Xaa Phe Xaa Leu Xaa
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: This is an
      analog of substance P
<220> FEATURE:
<221> NAME/KEY: MOD_RES
<222> LOCATION: (2)
<223> OTHER INFORMATION: Xaa in position 2 is D-form of Proline;
<220> FEATURE:
<221> NAME/KEY: MOD_RES
<222> LOCATION: (7)
<223> OTHER INFORMATION: Xaa in position 7 is D-form of Phenylalanine;
<220> FEATURE:
<221> NAME/KEY: MOD_RES
<222> LOCATION: (9)
<223> OTHER INFORMATION: Xaa in position 9 is D-form of Tryptophan;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lavielle, et al.
<303> JOURNAL: Biochem. Pharmacol.
<304> VOLUME: 37
<306> PAGES: 41-
<307> DATE: 1988
<300> PUBLICATION INFORMATION:
<301> AUTHORS: Quirion, R.
       Dam, T.V.
<303> JOURNAL: Regulatory Peptides
<304> VOLUME: 22
<306> PAGES: 18-
<307> DATE: 1988

<400> SEQUENCE: 15

Arg Xaa Lys Pro Gln Gln Xaa Phe Xaa Leu Met Gly
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: This is an
      analog of substance P
```

-continued

```
<220> FEATURE:
<221> NAME/KEY: MOD_RES
<222> LOCATION: (2)
<223> OTHER INFORMATION: Xaa in position 2 is D-form of Proline;
<220> FEATURE:
<221> NAME/KEY: MOD_RES
<222> LOCATION: (7)
<223> OTHER INFORMATION: Xaa in position 7 is D-form of Tryptophan;
<220> FEATURE:
<221> NAME/KEY: MOD_RES
<222> LOCATION: (9)
<223> OTHER INFORMATION: Xaa in position 9 is D-form of Tryptophan;
<220> FEATURE:
<221> NAME/KEY: MOD_RES
<222> LOCATION: (11)
<223> OTHER INFORMATION: Xaa in position 11 is Methionine amide;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lavielle, et al.
<303> JOURNAL: Biochem. Pharmacol.
<304> VOLUME: 37
<306> PAGES: 41-
<307> DATE: 1988
<300> PUBLICATION INFORMATION:
<301> AUTHORS: Quirion, R.
       Dam, T.V.
<303> JOURNAL: Regulatory Peptides
<304> VOLUME: 22
<306> PAGES: 18-
<307> DATE: 1988

<400> SEQUENCE: 16

Arg Xaa Lys Pro Gln Gln Xaa Phe Xaa Leu Xaa
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: This is an
      analog of substance P
<220> FEATURE:
<221> NAME/KEY: MOD_RES
<222> LOCATION: (2)
<223> OTHER INFORMATION: Xaa in position 2 is D-form of Proline;
<220> FEATURE:
<221> NAME/KEY: MOD_RES
<222> LOCATION: (7)
<223> OTHER INFORMATION: Xaa in position 7 is D-form of Tryptophan;
<220> FEATURE:
<221> NAME/KEY: MOD_RES
<222> LOCATION: (9)
<223> OTHER INFORMATION: Xaa in position 9 is D-form of Tryptophan;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lavielle, et al.
<303> JOURNAL: Biochem. Pharmacol.
<304> VOLUME: 37
<306> PAGES: 41-
<307> DATE: 1988
<300> PUBLICATION INFORMATION:
<301> AUTHORS: Quirion, R.
       Dam, T.V.
<303> JOURNAL: Regulatory Peptides
<304> VOLUME: 22
<306> PAGES: 18-
<307> DATE: 1988

<400> SEQUENCE: 17
```

```
Arg Xaa Lys Pro Gln Gln Xaa Phe Xaa Leu Met Gly
 1               5               10
```

```
<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: This is an
      analog of substance P.
<220> FEATURE:
<221> NAME/KEY: MOD_RES
<222> LOCATION: (11)
<223> OTHER INFORMATION: Xaa at position 11 is Methionine amide;
<300> PUBLICATION INFORMATION:
<310> PATENT DOCUMENT NUMBER: 5891842
<311> PATENT FILING DATE: 1996-04-12
<312> PUBLICATION DATE: 1999-04-16
<300> PUBLICATION INFORMATION:
<301> AUTHORS: Lavielle, et al.
<303> JOURNAL: Biochem. Pharmacol.
<304> VOLUME: 37
<306> PAGES: 41-
<307> DATE: 1988
<300> PUBLICATION INFORMATION:
<301> AUTHORS: Quirion, R.
       Dam, T.V.
<303> JOURNAL: Regulatory Peptides
<304> VOLUME: 22
<306> PAGES: 18-
<307> DATE: 1988

<400> SEQUENCE: 18

Arg Pro Cys Pro Gln Cys Phe Tyr Gly Pro Xaa
 1               5               10
```

What is claimed is:

1. A method for treating neurogenic inflammation pain, the method comprises injecting a therapeutically effective amount of about 0.01 units to about 1,000 units of an agent to a patient, the agent comprising the light chain of a *botulinum* toxin covalently coupled to the $H_N$ portion of the heavy chain of the *botulinum* toxin, and a substance P component covalently coupled to the *botulinum* toxin $H_N$ portion, the substance P component being effective in binding to a substance P receptor, thereby treating the neurogenic inflammation pain for at least about two months.

2. The method of claim 1 wherein the *botulinum* toxin light chain is the light chain of a *botulinum* toxin selected from the group consisting of *botulinum* toxin serotype A, serotype B, serotype C, serotype D, serotype E, serotype F and serotype G.

3. The method of claim 1 wherein the *botulinum* toxin $H_N$ portion is the $H_N$ portion of a *botulinum* toxin selected from the group consisting of *botulinum* toxin serotype A, serotype B, serotype C, serotype D, serotype E, serotype F and serotype G.

4. The method of claim 2 wherein the light chain is a light chain of a *botulinum* toxin serotype A.

5. The method of claim 3 wherein the $H_N$ portion is an $H_N$ portion of a *botulinum* toxin serotype A.

6. The method of claim 1 wherein the substance P component is substance P.

7. The method of claim 1 wherein the pain is arthritis pain.

8. The method of claim 1 wherein the agent is injected subcutaneously.

9. The method of claim 1 wherein the agent is injected intramuscularly.

10. The method of claim 1 wherein the agent is injected in an amount from about $10^{-2}$ U/kg to about 100 U/kg.

11. The method of claim 1 wherein the agent is injected in an amount from about $10^{-1}$ U/kg to about 10 U/kg.

12. The method of claim 1 wherein the agent is injected in an amount from about 1 unit to about 20 units.

13. The method of claim 1 wherein the agent is injected in an amount from about 1 unit to about 10 units.

14. The method of claim 1 wherein the agent is injected in an amount from about 0.1 U/kg to about 30 U/kg.

* * * * *